United States Patent [19]

Schrader

[11] 4,168,620
[45] Sep. 25, 1979

[54] METHOD FOR TESTING IMPACT STRENGTH

[76] Inventor: Ernest K. Schrader, 1255 Magnolia Dr., Walla Walla, Wash. 99362

[21] Appl. No.: 876,572

[22] Filed: Feb. 10, 1978

[51] Int. Cl.² .............................................. G01N 3/34
[52] U.S. Cl. ........................................ 73/12; 73/803
[58] Field of Search ................ 73/12, 82, 88 C, 87, 73/810, 808, 803

[56] References Cited

U.S. PATENT DOCUMENTS

| | | | |
|---|---|---|---|
| 161,737 | 4/1875 | Beardslee | 73/12 X |
| 1,348,897 | 8/1920 | Ringland | 73/82 |
| 1,457,015 | 5/1923 | Besson | 73/12 |
| 1,604,141 | 10/1926 | Amsler | 73/12 |
| 2,359,044 | 9/1944 | MacBride | 73/101 |
| 2,579,503 | 12/1951 | Lubin et al. | 73/12 |
| 3,056,279 | 10/1962 | Milewski et al. | 73/35 |
| 3,266,289 | 8/1966 | Stamy | 73/12 |
| 3,488,991 | 1/1970 | Dietert et al. | 73/12 |
| 3,859,841 | 1/1975 | Evans et al. | 73/12 |
| 3,999,420 | 12/1976 | Wright | 73/12 |

*Primary Examiner*—Charles A. Ruehl
*Attorney, Agent, or Firm*—Henderson & Sturm

[57] ABSTRACT

A method and apparatus for testing the impact strength of materials which is especially effective for testing the impact strength of fiber reinforced concrete.

1 Claim, 5 Drawing Figures

U.S. Patent  Sep. 25, 1979  4,168,620
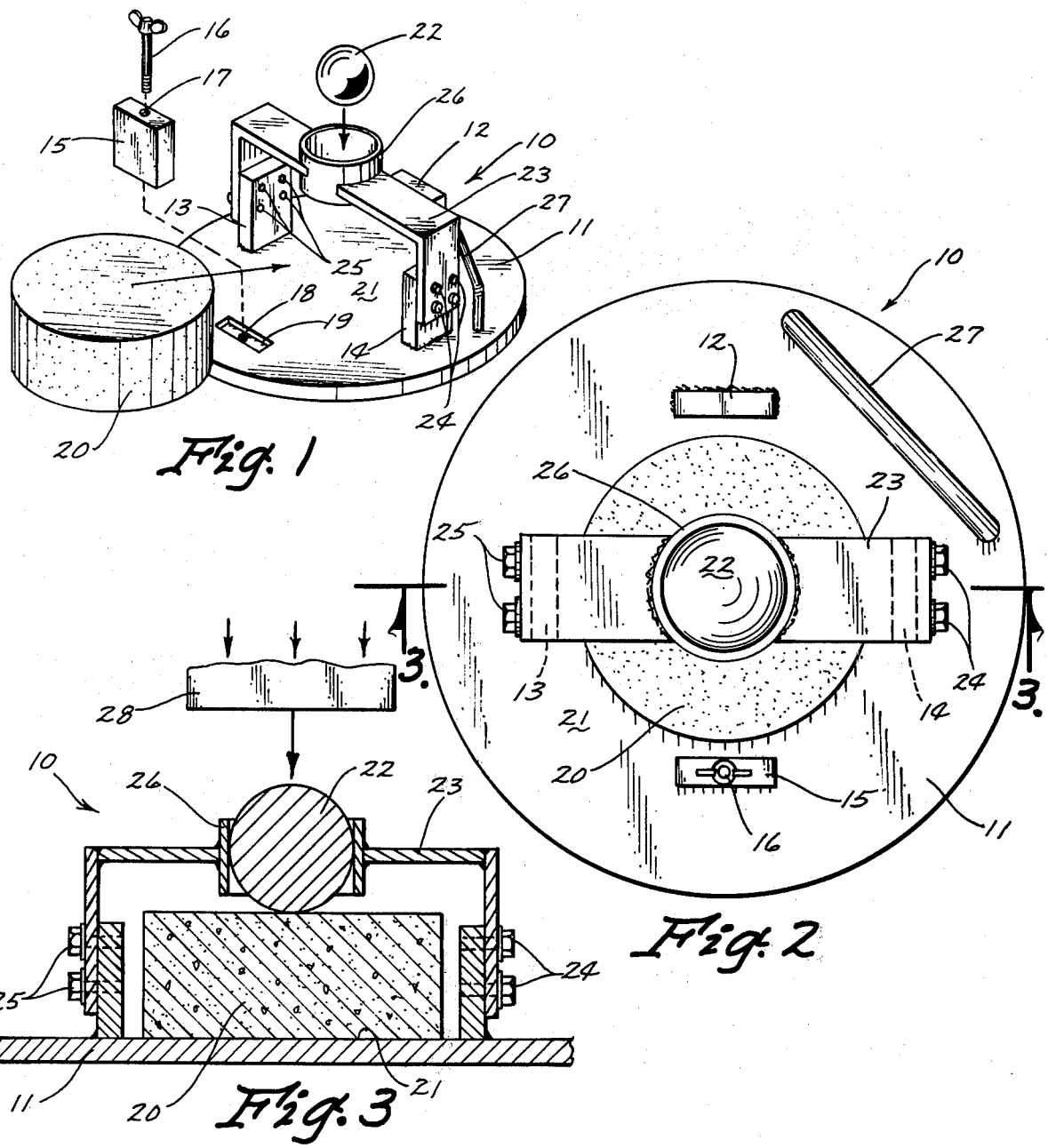

METHOD FOR TESTING IMPACT STRENGTH

BACKGROUND OF THE INVENTION

The use of fiber reinforced concrete (FRC) has passed from purely experimental laboratory scale applications into factory and field applications involving the placement of many thousands of cubic yards annually throughout the world.

Experience has indicated the advisability of modifying or creating new testing methods and procedures to insure reproducible meaningful results with these unique material systems. There has been an effort in the industry to standardize procedures and equipment so that results can be effectively evaluated and compared. There are adequate testing procedures for fiber reinforced concrete and the like for many properties such as the modulus of rupture, compressive strength, tensile strength, shrinkage, creep, modulus of elasticity, etc., but there is a need for a better apparatus and method for testing and indexing the impact strength of such materials.

Impact strength is an important property of fiber-reinforced concrete. It can be used to compare the relative merits of different fiber concrete mixes or to demonstrate the improved performance of a fiber mix when compared to a conventional concrete mix. It can also be adapted, if desired, to show the relative impact resistance of different thicknesses of material.

One of the major material properties of fibrous concrete is its tremendous impact resistance when compared to conventional concrete. There are only a couple of methods that are presently available for testing or analyzing any material for impact and these are not useful for concrete, for example the Charpy and Izod tests. The Charpy equipment uses a large swinging pendulum which strikes a notched test specimen. The distance that the pendulum travels after breaking the specimen is a measure of impact resistance. This equipment is not applicable to concrete since very large samples would be required. The equipment is expensive, heavy, large, non-portable and requires a rigid base for mounting. The Izod method has been used in Europe for evaluating impact resistance and it involves subjecting a test specimen to an impact load after which its internal micro-cracking is analyzed with ultrasonic sound wave equipment and an oscilloscope. Neither of these methods are practical, economical, or portable and the latter test requires technicians which are highly trained. Consequently, there is a need for a method and apparatus of testing impact strength to overcome these disadvantages.

SUMMARY OF THE INVENTION

The present invention relates to a method and apparatus for testing the impact strength of a sample of material. The apparatus used for such testing includes a base plate having a sample receiving surface. A plurality of restraint lugs are attached to the base surrounding and spaced from the sample receiving surface. An impact transmitting mechanism is disposed above the sample surface for contacting the sample and being movable upon impact towards the sample. A supporting structure is attached to the apparatus for holding the impact transmitting mechanism substantially centrally located with respect to the sample receiving surface. An impact mechanism is also provided for forcing the impact transmitting mechanism against the sample. The method for using this apparatus comprises the steps of causing the impact mechanism to strike the impact transmitting mechanism with an equal force for a plurality of times until the sample is forced in contact with all of the restraint lugs and recording the number of times that the impact mechanism is utilized to cause the sample to be in contact with all of the restraint lugs thereby providing an impact strength index.

An object of the present invention is to provide an improved method and apparatus for testing the impact strength of a material.

Another object of the invention is to provide a meaningful standard impact strength index for fibrous concrete materials.

A further object of the invention is to provide impact strength testing equipment which is portable.

Still another object of the invention is to provide an apparatus for testing impact strength which is practical to use and economical to produce.

A still further object is to provide an apparatus for testing the impact strength of materials which is dependable and simple to use, thereby obviating the need for highly skilled technicians.

Other objects, advantages and novel features of the invention will become apparent from the following detailed description of the invention when considered in conjunction with the accompanying drawings.

BRIEF DESCRIPTION OF THE DRAWINGS

FIG. 1 is a perspective exploded view of the impact strength testing apparatus of the present invention;

FIG. 2 is a top plan view of the apparatus shown in FIG. 1; and

FIG. 3 is a cross-sectional view taken along line 3—3 of FIG. 2.

DESCRIPTION OF THE PREFERRED EMBODIMENT

Referring now to the drawings wherein like reference numerals designate identical or corresponding parts throughout the several views, FIG. 1 shows an impact strength testing device 10 constructed in accordance with the present invention. A rigid base plate 11 has three upstanding restraint lugs 12, 13 and 14 welded thereto. A fourth restraint lug 15 is removably attached to the base plate 11 by means of a bolt 16 which extends through a hole 17 in the restraint lug 15, and which bolt 16 is threadably received in an opening 18 in the base plate 11. The threaded hole 18 is in a depression 19 formed in the plate 11 for the purpose of receiving the lower portion of the restraint lug 15 and thereby further supporting such restraint lug. A sample of material such as fiber reinforced concrete 20 is cut to a size wherein it can be received on a sample receiving surface 21 on the base plate 11 and still be spaced from the restraint lugs 12-15.

An impact transmitter in the form of a hardened steel ball 22 is disposed above and rests upon the sample 20 as can best be seen in FIG. 3. This impact transmitter 22 is held centrally located above the sample receiving surface by supporting structure including an upper U-shaped bracket 23 which is attached to the lugs 13 and 14 by means of bolts 24 which are threadably received into openings 25 in the restraint lugs 13 and 14. Centrally disposed on the upper bracket 23 is a cylinder 26 which serves to guide the impact transmitter ball 22 to prevent it from rolling off on the top of the sample 20 and yet allow it to freely contact the sample 20 in a vertical direction. A handle 27 of a U-shaped configuration is welded at the ends thereof to the rigid base plate 11 for facilitating the movement of the apparatus 10 from place to place and enhancing the portable nature of the invention.

Referring to FIG. 3, it is noted that a compaction hammer 28 is provided for forcing the impact transmitter 22 against the sample 20. This compaction hammer could, for example, be a standard ten pound compaction hammer with an eighteen inch drop and the impact transmitter could, for example, be a hardened steel ball which is 2½ inches in diameter.

The sample 20 can be constructed in a number of ways, but it is preferably constructed by use of a standard 6-inch mold which is filled to the 2½ inch thick level. These test specimens should be prepared, whenever possible, using external vibrations only. Internal vibration is not desirable and rodding is not acceptable, since these methods of consolidation may produce fiber orientation effects and non-uniform samples. When necessary, an external vibrator can be held against the outside of the form to provide consolidation of small specimens. Test specimens having a dimension of 4-inches or less should be made in a single lift to avoid fiber orientation effects or fiber-free planes. The type, size and amount of fiber should be reported. All fiber contents should be reported on the basis of percentage of total fiber volume to total concrete volume unless otherwise specified in the test results. Also, the coefficient of variation of test results should be reported. The concrete samples are made in molds using compressive cylinders but using only one lift.

Specimens should be tested at 7, 28 and 90 days of age, for example. The curing and handling of the specimens should be similar to those used for compressive cylinders. Prior to testing, the samples are removed from the molds and the same procedures are followed as would be followed for the preparation of compressive cylinders for testing. The thickness of the specimens needs to be recorded to the nearest one-sixteenth of an inch. The reported thickness is to be determined by averaging the measured distance at the center and at each edge of the specimen along any diameter across the top surface. The samples are then placed on the base plate within the positioning lugs by having first removed the restraint lug 15, slipping the sample 20 into place and then repositioning the restraint lug 15 by slipping it into the opening 19 and engaging the bolt 16 within the threaded opening 18.

The positioning bracket 23 is then bolted in place and the hardened steel ball 22 is placed on top the specimen within the bracket cylinder 26. The drop hammer is placed with its base upon the steel ball and held there with just enough downward pressure to keep it from bouncing off the ball during the test. The base plate is set solidly on a rigid floor, and the person performing the test is to stand with both feet on the base plate. The hammer is dropped consecutively and the number of blows required to cause the first visible crack on the top of the sample 20 is recorded. The hammer is then again dropped consecutively until the sample has yielded to the point that it is in contact with all four of the restraint lugs 12–15. Then the total number of blows of the hammer is recorded to indicate how many blows it required to cause the ultimate failure of the sample. Ultimate failure is defined as the number of blows required to open the cracks in the specimens sufficiently so that the pieces of concrete are touching each of the four positioning lugs 12–15 on the base plate. This procedure can be mechanized if desired in a manner which is well known in the soil compaction art.

If the specimen breaks into two pieces during this testing procedure, failure results may vary considerably with the different types of mixes, fiber contents, etc. However, an example of results that might be experienced is as follows. At seven days of age a conventional ¾ inch aggregate concrete mix may exhibit a first crack at 30 blows and an ultimate failure at 32 blows. A fibrous concrete mix may exhibit a first crack at 45 blows and an ultimate failure at 75 blows or greater.

It is to be understood that the height of the bracket 23 is adjustable by virtue of the two levels of holes 25 for reception of bolts 24 and that other height adjusting structures could obviously be used.

Consequently, it can be appreciated from the explanation above that this apparatus 10 and the methods of using it can provide a very meaningful index for the impact strength of a material such as a fibrous concrete material. The two indexes referred to above are, of course, only examples and others could be used and still be within the scope of this invention; but, it is noted that the index of what is required to produce the beginning of a crack in a specimen corresponds to the number of blows of the compaction hammer 28 to cause such crack and the index for ultimate failure of a specimen corresponds to the number of blows required to cause the specimen to contact all four of the restraint lugs 12–15.

Obviously many modifications and variations of the present invention are possible in light of the above teachings. It is therefore to be understood that, within the scope of the appended claims, the invention may be practiced otherwise than as specifically described.

I claim:
1. A method of testing impact strength of a sample using an apparatus comprising:
   a base plate including a sample receiving surface;
   a sample disposed on said sample receiving surface;
   a plurality of restraint lugs attached to said base plate surrounding said sample and spaced from said sample;
   impact transmitting means disposed above said sample surface for contacting said sample and being movable upon impact towards said sample;
   support means attached to said apparatus for holding said impact transmitting means substantially centrally located with respect to said sample receiving surface; and
   impact means for forcing said impact transmitting means against said sample; said method comprising:
   causing said impact means to impact said impact transmitting means with an equal force for a plurality of times until said sample is in contact with each of said restraint lugs; and
   recording the number of times that said impact means is utilized to cause the sample to be in contact with all of the restraint lugs thereby providing an impact strength index.

* * * * *